(12) United States Patent
Breske et al.

(10) Patent No.: US 12,090,332 B2
(45) Date of Patent: *Sep. 17, 2024

(54) MULTI-SENSORY ALARM FOR A WEARABLE CARDIAC DEFIBRILLATOR

(71) Applicant: WEST AFFUM HOLDINGS DAC, Dublin (IE)

(72) Inventors: Pamela F. Breske, Newcastle, WA (US); Zoie R. Engman, Kirkland, WA (US); Judy Reed Edworthy, Tiverton (GB); Amanda K. Hall, Seattle, WA (US)

(73) Assignee: WEST AFFUM HOLDINGS DAC, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 17/547,641

(22) Filed: Dec. 10, 2021

(65) Prior Publication Data
US 2022/0096851 A1 Mar. 31, 2022

Related U.S. Application Data

(63) Continuation of application No. 16/394,979, filed on Apr. 25, 2019, now Pat. No. 11,198,015.
(Continued)

(51) Int. Cl.
*A61N 1/00* (2006.01)
*A61B 5/00* (2006.01)
*A61N 1/39* (2006.01)

(52) U.S. Cl.
CPC ............ *A61N 1/3904* (2017.08); *A61B 5/746* (2013.01); *A61N 1/3993* (2013.01);
(Continued)

(58) Field of Classification Search
CPC .. A61N 1/3904; A61N 1/3993; A61N 1/3918; A61N 1/3925; A61B 5/746;
(Continued)

(56) References Cited

U.S. PATENT DOCUMENTS 3,724,355 A 4/1973 Busch et al.
4,583,524 A 4/1986 Hutchins
(Continued)

FOREIGN PATENT DOCUMENTS

DE 2005060985 A2 6/2007
EP 2305110 A1 4/2011
(Continued)

OTHER PUBLICATIONS

Heartstart MRx and XL AED Algorithm—Application Note, Jul. 2001, Edition 2 Philips Healthcare, USA.
(Continued)

*Primary Examiner* — Scott M. Getzow
(74) *Attorney, Agent, or Firm* — Polsinelli PC

(57) ABSTRACT

In one embodiment, a wearable cardioverter defibrillator (WCD) is described. The WCD includes a support structure that may be worn by a patient. A processor is coupled to the support structure. The wearable cardioverter defibrillator also includes a discharge circuit configured to discharge a stored electrical charge through a body of the patient, the discharge circuit in communication with the processor. The processor may be configured to detect an event occurring at the WCD and determine a severity of the event occurring at the WCD. The processor may activate a multi-sensory alarm based at least in part on the determined event severity.

20 Claims, 8 Drawing Sheets

Related U.S. Application Data

(60) Provisional application No. 62/662,899, filed on Apr. 26, 2018.

(52) U.S. Cl.
CPC .......... *A61B 5/4836* (2013.01); *A61B 5/6823* (2013.01); *A61B 5/7203* (2013.01); *A61N 1/3918* (2013.01); *A61N 1/3925* (2013.01)

(58) Field of Classification Search
CPC ... A61B 5/4836; A61B 5/6823; A61B 5/7203; A61B 5/361; A61B 5/7282; A61B 5/7405; A61B 5/742; A61B 5/7455
See application file for complete search history.

(56) References Cited

U.S. PATENT DOCUMENTS

| | | | |
|---|---|---|---|
| 4,619,265 A | 10/1986 | Morgan et al. | |
| 4,666,432 A | 5/1987 | McNeish et al. | |
| 4,698,848 A | 10/1987 | Buckley | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,429,593 A | 7/1995 | Matory | |
| 5,474,574 A | 12/1995 | Payne et al. | |
| 5,618,208 A | 4/1997 | Crouse et al. | |
| 5,662,690 A | 9/1997 | Cole et al. | |
| 5,708,978 A | 1/1998 | Johnsrud | |
| 5,741,306 A | 4/1998 | Glegyak et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 | 8/2001 | Glegyak et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,450,942 B1 | 9/2002 | Lapanashvili et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,753,759 B2 | 7/2010 | Pintor et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,527,028 B2 | 9/2013 | Kurzweil et al. | |
| 8,548,557 B2 | 10/2013 | Garstka et al. | |
| 8,560,044 B2 | 10/2013 | Kurzweil et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,706,255 B2 | 4/2014 | Phillips et al. | |
| 8,742,349 B2 | 6/2014 | Urbon et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| 9,265,432 B2 | 2/2016 | Warren et al. | |
| 9,345,898 B2 | 5/2016 | Piha et al. | |
| 9,408,548 B2 | 8/2016 | Volpe et al. | |
| 9,445,719 B2 | 9/2016 | Libbus et al. | |
| 9,454,219 B2 | 9/2016 | Volpe et al. | |
| 9,579,020 B2 | 2/2017 | Libbus et al. | |
| 9,592,403 B2 | 3/2017 | Sullivan | |
| 9,598,799 B2 | 3/2017 | Shoshani et al. | |
| 9,675,804 B2 | 6/2017 | Whiting et al. | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,192,387 B2 | 1/2019 | Brinig et al. | |
| 10,307,133 B2 | 6/2019 | Kaib | |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 2002/0181680 A1 | 12/2002 | Linder et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Vollpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0165809 A1* | 6/2013 | Abir | A61B 5/113 600/534 |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0307685 A1 | 11/2013 | Sholder | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |
| 2015/0297135 A1 | 10/2015 | Shoshani et al. | |
| 2015/0328472 A1 | 11/2015 | Sullivan et al. | |
| 2016/0004831 A1 | 1/2016 | Carlson et al. | |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |

(56) References Cited

U.S. PATENT DOCUMENTS

| | | |
|---|---|---|
| 2016/0113581 A1 | 4/2016 | Amir et al. |
| 2016/0256104 A1 | 9/2016 | Romem et al. |
| 2016/0283900 A1 | 9/2016 | Johnson et al. |
| 2016/0328529 A1* | 11/2016 | Kaib ................ G16H 40/40 |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0144600 A1* | 5/2018 | Grubis ................ A61B 5/746 |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | | |
|---|---|---|---|
| JP | 4320257 | A | 3/2005 |
| JP | 5963767 | A | 1/2014 |
| JP | 2014526282 | A | 10/2014 |
| WO | 98/39061 | A2 | 9/1998 |
| WO | 2011/146448 | A1 | 11/2011 |
| WO | 2012/064604 | A1 | 5/2012 |
| WO | 2012/151160 | A1 | 11/2012 |
| WO | 2015/056262 | A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

\* cited by examiner

US 12,090,332 B2

MULTI-SENSORY ALARM FOR A WEARABLE CARDIAC DEFIBRILLATOR

CROSS-REFERENCE TO RELATED APPLICATION

This application is a continuation of U.S. application Ser. No. 16/394,979, filed Apr. 25, 2019, which claims the benefit of U.S. Provisional Application No. 62/662,899 filed Apr. 26, 2018, the disclosures of which are hereby incorporated by reference herein in their entirety for all purposes.

BACKGROUND

Heart arrhythmias may reduce blood flow to various parts of the body. In some instances, arrhythmias result in a Sudden Cardiac Arrest (SCA) where a person's heart suddenly and unexpectedly stops beating. If this occurs, blood may stop flowing to the brain and other vital organs. SCA can lead to death very quickly, within minutes, unless action is taken quickly.

Some people have an increased risk of SCA. This includes people who have had a heart attack, a prior SCA episode, among other risk factors. Frequently, these people are recommended for an Implantable Cardioverter Defibrillator ("ICD"). The ICD is a small electronic device connected to the heart that continuously monitors the person's electrocardiogram ("ECG"). If or when the ICD detects certain types of heart arrhythmias or abnormalities, then the ICD delivers an electric pulse or shock to the heart.

A patient may have a period of time between being recommended for an ICD and actually receiving one. In the interim timeframe, a patient may be suited with a wearable cardioverter defibrillator ("WCD") system. A WCD system is worn by the patient and includes, among other components, a defibrillator and one or more external electrodes. When a patient wears a WCD system, the WCD may monitor several patient parameters, including the patient's ECG. If a potentially life-threatening arrhythmia is detected, the defibrillator may be activated and primed to deliver an appropriate electric shock through the patient's body which also shocks the heart.

When a patient is given a WCD, the WCD may issue alarms to the patient for specific detected events. The alarm provides the patient with an opportunity to override the electric shock in case the WCD has misdiagnosed a shockable rhythm, which may occur for various reasons. However, a single alarm may go unnoticed. The alarm may not be loud enough to gain the patient's attention or a vibration alarm may go undetected by the patient.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, a wearable cardioverter defibrillator (WCD) is described. The WCD includes a support structure that may be worn by a patient. A processor is coupled to the support structure. The wearable cardioverter defibrillator also includes a discharge circuit configured to discharge a stored electrical charge through a body of the patient, the discharge circuit in communication with the processor. The processor may be configured to detect an event occurring at the WCD and determine a severity of the event occurring at the WCD. The processor may activate a multi-sensory alarm based at least in part on the determined event severity.

In some embodiments, the multi-sensory alarm may be a combination of at least two of a visual alarm, audible alarm, and haptic alarm. A patient alert button may be coupled to the support structure. In some embodiments, the patient alert button may include an audible output and a patient input button. The WCD may also include a communication device coupled to the support structure wherein the communication device includes an alarm module and a monitor, light, haptic motor, and audible output in communication with the alarm module. In some embodiments, the multi-sensory alarm includes of a visual alarm, a haptic alarm, and an audible alarm. In some embodiments, the processor is further configured to synchronize the visual alarm, haptic alarm, and audible alarm to harmonize the alarm output. In some embodiments, the audible alert includes a combination of a voice alert and a tone. In some instances, the visual alarm includes at least one of a blinking light, a written message, or an image. In some embodiments, the audible alarm varies in at least one of a pitch, tone, or timbre based at least in part on the severity of the multi-sensory alarm.

In one embodiment, a WCD system is described. The WCD may include a support structure for wearing by a patient. The WCD also may include a defibrillator housing coupled to the support structure and a discharge circuit in communication with the defibrillator housing. The discharge circuit may be configured to discharge a stored electrical charge through a body of the patient. The WCD may also include a processor within the defibrillator housing, the processor in communication with the discharge circuit. At least one communication device may be in communication with the processor. The communication device may include a visual output, an audible output, and a haptic output. The processor may be configured to detect an event occurring at the WCD and determine a severity of the event occurring at the WCD. The processor may activate a multi-sensory alarm at the communication device based at least in part on the determined event severity.

In a further embodiment, a WCD system may include a support structure for wearing by a patient. The WCD may include one or more electrodes for delivering a charge to the patient while the patient is wearing the support structure. A discharge circuit may be coupled to the electrodes, the discharge circuit configured to store an electrical charge. The WCD may include a processor for activating the discharge circuit, the processor in communication with the discharge circuit. At least one physiological sensor module may be in communication with the processor. The at least one physiological sensor module may be configured to monitor a physiological parameter of the patient while the patient wears the support structure and to transmit a first signal that communicates the physiological parameter. The WCD system may include at least one motion sensor module in communication with the processor, the at least one motion sensor module configured to monitor a motion parameter of the patient while the patient wears the support structure and to transmit a second signal that communicates the motion parameter.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest. When a patient wears a WCD, it may need to alert the patient throughout its use. However, the patient may not be alerted without some sort of alert mechanism. For example, the patient may not check the status of the WCD system during regular intervals and may require an alert to gain their attention. This is especially true when the status of the WCD is critical or there is an impending shock. However, some alerts may not be commanding enough for the situation while other alerts may be too commanding. Therefore, the present disclosure relates to a system and method for gaining the attention of the patient in manners relating to the severity of the situation.

Figure 1:
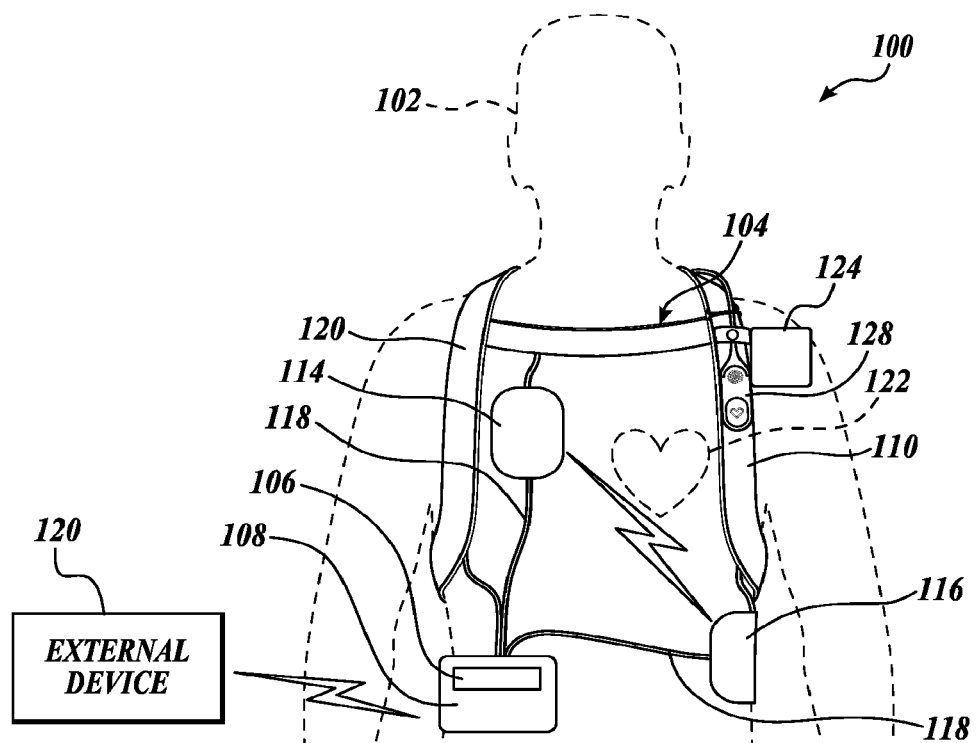
FIG. 1 is a diagram of a sample WCD system in accordance with the present disclosure.

FIG. 1 illustrates a system 100 with a patient 102 wearing an example of a WCD system 104 according to embodiments described herein. The WCD system may include one or more communication devices 106, a support structure 110, an external defibrillator 108 connected to defibrillation electrodes 114, 116, among other components.

The support structure 110 may be worn by the patient 102. The support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap, or may be kept close to the patient 102 such as in a cart, bag, stroller, wheelchair, or other vehicle.

The external defibrillator 108 may be coupled to the support structure 110 or may be carried remotely from the patient 102. The external defibrillator 108 may be triggered to deliver an electric shock to the patient 102 when patient 102 wears WCD system 104. For example, if certain thresholds are exceeded or met, the external defibrillator 108 may be engaged and deliver a shock to the patient 102.

The WCD system 104 may defibrillate the patient 102 by delivering an electrical charge to the patient 102 through a series of electrodes 114, 116 positioned on the torso 112. The electrodes 114, 116 may be electrically coupled to the external defibrillator 108 via a series of electrode leads 118. The defibrillator 108 may administer an electric shock to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116. The electric shock may be a defibrillation shock, which may go through a heart 122 of the patient 102 in an attempt to restart the heart 122. The brief, strong electric pulse may work to restart the heart 122 which may save the patient's life.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include physical state of the patient 102 such as ECG, movement, heartrate, pulse, temperature, and the like. Local parameters may also include a parameter of the WCD 104, environmental parameters, or the like. The monitoring device 124 may be physically coupled to the support structure 110 or may be proximate the support structure 110. In either location, the monitoring device 124 is communicatively coupled with other components of the WCD 104.

In some embodiments, a communication device 106 may enable the patient to interact with, and garnish data from, the WCD system 104. The communication devices 106 may enable a patient or third party to view patient data, dismiss a shock if the patient is still conscious, turn off an alarm, and otherwise engage with the WCD system 104. In some embodiments, the communication device 106 may be a separable part of an external defibrillator 108. For example, the communication device 106 may be a separate device coupled to the external defibrillator 108. In this embodiment, the communication device 106 may be wired, or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device. For example, the defibrillator 108 may include components able to communicate to the patient and the WCD system 104 may include a separate communication device 106 remote from the defibrillator 108.

In some embodiments, the communication device 106 may be communicatively coupled to an alert button 128. The alert button 128 may be removably coupled to the support structure 110. The patient 102 may couple the alert button 128 to the support structure 110 or may couple the alert button 128 to an article of clothing. The alert button 128 may be wiredly or wirelessly connected to the communication device 106.

In some embodiments, the communication device 106 or the defibrillator 108 may connect with one or more external devices 124. For example, as shown in FIG. 1, the communication device 106 or the defibrillator 108 may connect to various external devices 120 such as a cloud, a remote desktop, a laptop, a mobile device, or other external device using a network such as the Internet, local area networks, wide area networks, virtual private networks (VPN), other communication networks or channels, or any combination thereof.

Figure 2:
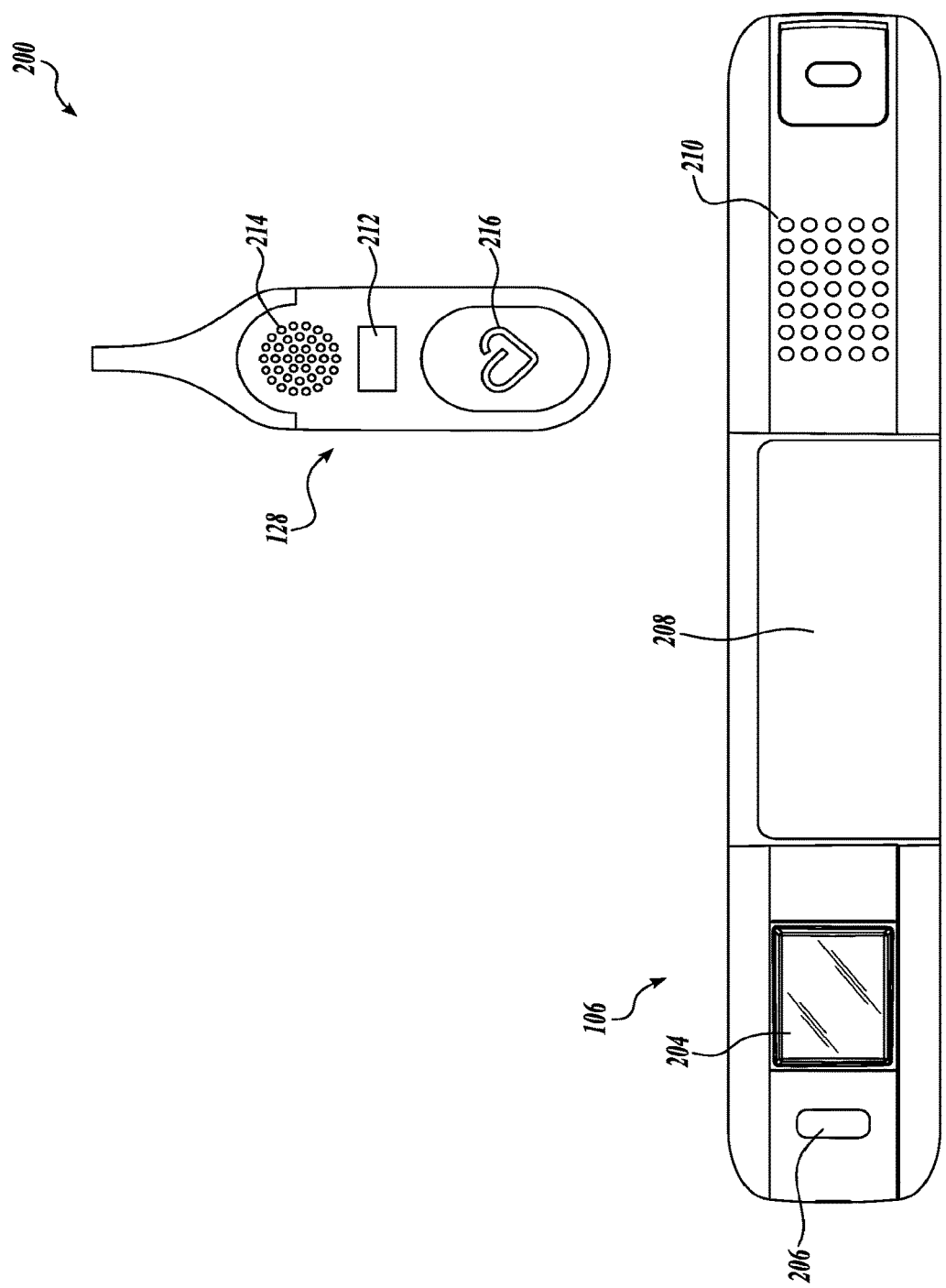
FIG. 2 is a diagram of an example communication system shown in FIG. 1.

FIG. 2 is an example of a communication system 200 according to embodiments described herein. The communication system 200 may include a communication device 106 and an alert button 128. The communication device 106 may be a part of the defibrillator 108 or may be a separate device. The alert button 128 may be wired or wirelessly connected to the communication device 106.

The communication device 106 may include a screen 204, a visual indicator 206, a battery 208, and an audio output 210. The screen 204 may include any variation of a screen to display text and images to a patient and/or user. For example, the screen may be an LED display, plasma display panel (PDP), liquid crystal display (LCD), organic light emitting diode display (OLED), e-paper, and the like. The screen may be monochromatic, that is, the screen may display in black, white, and grayscale, or the screen may be a color screen. The screen may display text, images, scrolling text, alerts, or some combination thereof. The screen may additionally be touch sensitive, allowing the user to interact directly with the communication device 106 by touching the screen 204. In other embodiments, the communication device 106 may include one or more input buttons (not shown).

The visual indicator 206 may include a single light source as shown or may include a number of light sources. The visual indicator 206 may use color and/or lighting patterns to communicate various alerts or conditions of the WCD system 104 to the patient or third party. The visual indicator 206 may include one or more multi-color LEDs which may be capable of emitting two or more different colors, or combinations of those colors. For example, the visual indicator 206 may comprise a red/green/blue (RBG) LED. The RBG LED may emit a red, blue, or green color. However, the RBG may also emit purple by engaging both the red and blue color. Other types of multi-color LEDs may also be used. When multiple visual indicators 206 are present, each visual indicator 206 may comprise either a single-color LED or a multi-color LED.

The lighting pattern of the visual indicator 206 may comprise a multitude of patterns. In some embodiments, the patterns may be simplistic for patient understanding. For example, a low-level alert or status may include a slow-blinking light pattern. A more urgent alert may be a medium-duration blinking light. Likewise, a fast-blinking alert may be an emergency or pressing situation. In some embodiments, the lighting pattern may follow a Morse code. This may enable a third party to recognize codes such as an SOS Morse code lighting pattern and determine the patient is in trouble. In some embodiments, the lighting pattern may change between various patterns. For example, if a shockable event is detected, the visual indicator 206 may emit a fast-blinking pattern. After a shock is delivered, the visual indicator 206 may change to an SOS lighting pattern to indicate the patient may need help.

The audio output 210 may include a speaker. The output of the audio output 210 may be loud enough to be heard over nominal background noise. For example, the audio output 210 may have a decibel output in the range of 35-90 dB (SPL). The output of the audio output 210 may be 1-8 watts. These ranges may be further narrowed. For example, if a patient has a hearing aid or reduced hearing capacity, the audio output 210 may be in a louder range such as 50-100 dB (SPL). In some embodiments, the audio output 210 might have an adjustable volume range. This may enable the patient to adjust the volume of the communication device 106 depending upon the patient's environment. In some embodiments, the communication device 106 may include a microphone (not shown). The microphone may detect ambient noise and automatically adjust the audio output 210 volume. This will help ensure the volume of the audio output 210 is at a preferred level for the particular patient and the particular setting. In some embodiments, the volume of the audio output 210 may increase as the alarm duration continues. For example, if a patient does not provide feedback to the communication device, the audio output 210 volume may increase to either gain the attention of the user or potentially alert bystanders or other third parties.

The alert button 128 may include a visual output 212, an audio output 214 and a user input 216. The visual output 212 may be similar to the visual output 206 of the communication device 106. Likewise, the audio output 214 may be similar to the audio output 210 of the communication device 106. The output of the audio output 214 may be loud enough to be heard over nominal background noise. For example, the audio output 214 may have a decibel output in the range of 35-90 dB(SPL). The output of the audio output 214 may be 1-8 watts. These ranges may be further narrowed. For example, if a patient has a hearing aid or reduced hearing capacity, the audio output 214 may be in a louder range such as 50-100 dB(SPL). In some embodiments, the audio output 214 might have an adjustable volume range. This may enable the patient to adjust the volume of the alert button 128 depending upon the patient's environment. In some embodiments, the alert button 128 may include a microphone (not shown). The microphone may detect ambient noise and automatically adjust the audio output 214 volume. This may ensure the volume of the audio output 214 is at a preferred level for the particular patient and the particular setting. In some embodiments, the audio output 214 of the alert button 128 may be coupled to the audio output 210. As the volume of audio output 210 is adjusted, either manually or automatically, the volume of the audio output 214 may be similarly adjusted. In some embodiments, the volume of the audio output 214 may increase as the alarm duration continues similar to the audio output 210.

Figure 3:
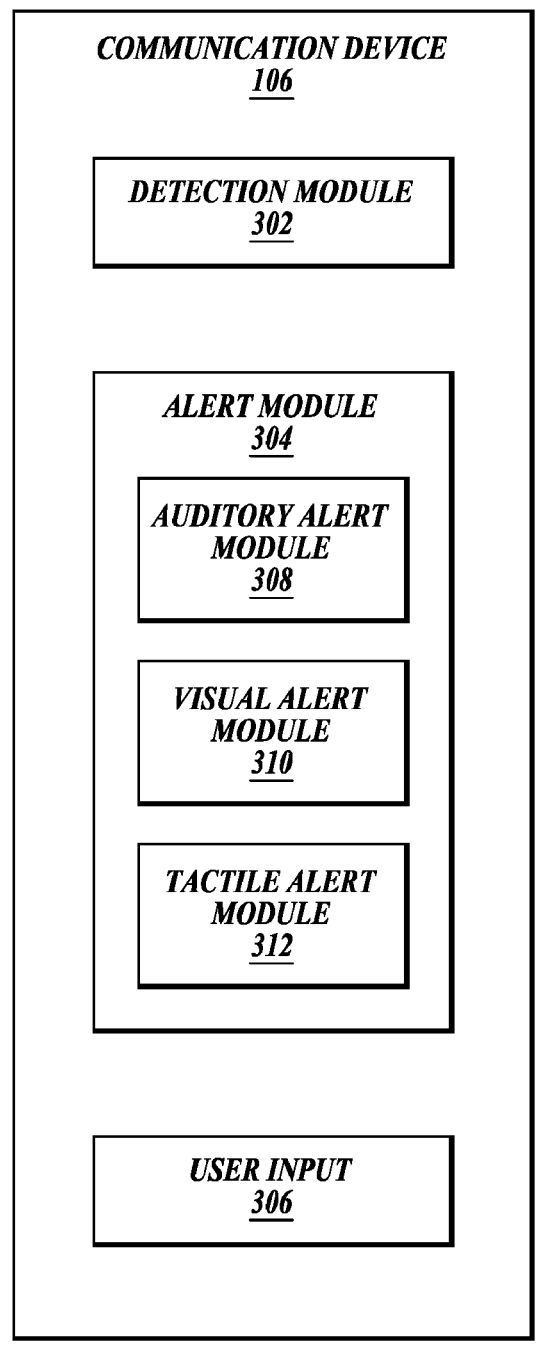
FIG. 3 is diagram of an example of a communication system in accordance with one example of present disclosure.

FIG. 3 is a block diagram illustrating functional components of one example of a communication device 106. The communication device 106 may be an example of the communication device 106 described with reference to FIGS. 1 and 2. In this example, the communication device 106 has detection module 302, an alert module 304, and a user input module 306. The alert module 304 may further include an auditory alert module 308, visual alert module 310, and a tactile alert module 312.

The detection module 302 may detect one or more conditions of the WCD system 104 or the patient 102. For example, the detection module 302 may be a logic device or algorithm to determine if any or a variety of thresholds are exceeded which may require action of the defibrillator 108. The detection module 302 may receive and interpret signals from an ECG port, a defibrillation port, and the like. The detection module 302 may process the information to ensure the patient is still conscious and healthy. The detection module 302 may additionally determine if the sensors, electrodes, and other system components are properly functioning. If any parameter indicates the patient 102 may be experiencing distress or a component of the WCD system 104 is malfunctioning, the detection module 340 may activate the alert module 304. In some embodiments, the detection module 302 may synchronize with another detection module proximate the defibrillator. In still further embodiments, the communication device 106 may be a part of the defibrillator 108 and utilize the same detection module 302.

The alert module 304 may receive an input from the detection module 302 and determine an alert threshold. The alert threshold may vary depending on the WCD mode, WCD state, and user-input responses. The alert module 304 may activate a multi-sensory alarm. The multi-sensory alarm may consist of a visual, auditory, and tactile alert. The alert module 304 may determine when and what sequence to provide visual, auditory, and tactile feedback. The alert module 304 may initially provide discreet feedback to the user and await a response, if no response is received, the alert module 304 may escalate the alert as necessary.

The auditory alert module 308 may provide a variety of audible alerts to the user. The audible alerts may include audio tones and voice messages. In some embodiments, the audio tones may comprise a short duration of harmonically rich tones. The tones may direct the patient's attention to the WCD system 104 where further messages may be displayed. A variety of different tones may be used to impart varying levels of alarm urgency. For example, the auditory alert module 308 may play the same series of tones but in varying pitches to denote varying levels of alarm urgency. The auditory alert module 308 may additionally change the tempo of the tones depending on the varying levels of alarm urgency. In still further embodiments, the actual tone might completely change depending on the alarm urgency. Each event may have a distinct alarm tone or each level of alarm may have a distinct alarm tone. In further embodiments, the auditory alert module 308 may change tempo and pitch of an alarm tone. In some embodiments, the patient may personalize the tones.

In some embodiments, the auditory alert module 308 may also change the volume of the audible alert. The alert may escalate in volume, pitch, tone, and/or timbre to gradually alert the patient. A gradual alarm approach may reduce patient anxiety and fear and allow the patient to calmly respond to the alarm. The duration of escalation may change depending on the urgency of the alert. A lower urgency alarm may have a slower rate of change whereas a high urgency alarm may have a much shorter duration but still gradually increase in pitch, tone, and/or volume.

The auditory alert module 308 may also provide voice messages. The voice messages may comprise informative messages to the patient, or potentially bystanders. The messages may include system alerts or patient health alerts. For example, if the patient is experiencing a cardiac event, the audible alert may announce the event in a loud tone to alert persons near the patient. This may enable the persons to take action such as CPR, or other first aid measures. The audible alert may additionally request further action such as a bystander to call an ambulance or other first responder. If the WCD system itself is experiencing maladies, the audible alert may be communicating such to the patient. This could include low battery alerts, poor connectivity, and the like. The voice messages and tones may layer over each other, for example, be played at the same time, or may alternate.

The auditory alert module 308 may utilize either the audio output 210 or the audio output 214 or both.

The visual alert module 310 may provide visual feedback to the user. This may be viewed as either a blinking light on the visual indicator 206 or may be an image or text displayed on the screen 204. The blinking light on the visual indicator 206 may mimic the auditory alert module 308. For example, the light may synchronize the tone being played by the auditory alert module 308. However, if the base tone remains the same throughout alarm urgency but changes in pitch and volume, the visual indicator 206 may not synchronize as the light cannot connote pitch and volume changes. Instead, the visual indicator may have a blinking light alert system where the frequency of the blinking changes with the urgency of the alarm. In still further embodiments, the blinking light alert may change to known communication mediums such as Morse code using an SOS blinking light pattern if an urgent, life threatening situation may arise.

The image or text may provide more detailed information to the patient. For example, if the battery is lower, a blinking no battery image may appear on the screen. Similarly, if an electrode is not connected properly, an electrode symbol may appear on the screen. If a shockable event is detected, a shock symbol may appear on the screen. In some embodiments, images and text may alternate to provide more complete information to the user. In still further embodiments, both image and text may appear on the screen.

The tactile alert module 312 may provide haptic feedback to the patient. The haptic feedback may present as vibrational patterns or waveforms emitting from the communication device 106, the alert button 128, or both. The haptic feedback may mimic the auditory alert module 308. For example, the haptic feedback might mimic the sound the auditory alert module 308 produces. The increase in pitch and tone may be translated to vibrational outputs. For example, the vibrations can match the length and intensity of a pitch and tone and gradually increase in strength as the alarm duration continues. In some embodiments, the tactile alert module 312 may output varying types of haptic response. For example, lower priority level alarms may result in short vibrational patterns. These short vibrational patterns may direct the patient's attention to lower priority events. High priority events such as high priority physiological conditions may result in escalating vibrations. The escalating vibrational pattern may have a longer time duration and begin gently but increase in intensity to quickly direct the patient's attention to the WCD system. As a high priority alarm continues without response, the time duration may shorten to eventually becoming a high vibrational pulse.

The user input module 306 may determine if user feedback is provided. For example, the patient may have a button (e.g., user input 216) proximate the alert button (e.g., alert button 128). When the alert module 304 triggers an alert, the patient may silence the alert via the user input device. The patient may be in a meeting, a public place, or some other location where the user does not wish for the alert to be heard.

The alert module 304 may receive an indication from the user input module 306 that the patient silenced an alarm. The alert module 304 then may take one of several actions. If the alert is a low urgency alert, the alert module 304 may snooze the alarm for a predetermined length of time. The predetermined length of time may vary depending upon the need for patient action. If the alert module 304 triggers a medium level alert, the alert module 304 may quiet the auditory alert module 308 preventing any sound output to the patient. However, the visual alert module 310 and the tactile alert module 312 may continue to alert the user as necessary. The auditory alert module 308 may activate again after a predetermined length of time.

If the alarm urgency is high, such as an indication of a cardiac event or an impending shock to the patient (or both), the alert module 304 may continue to operate modules 308, 310, 312 despite user input detected by the user input module 306. This may alert the patient or a bystander to an emergency situation requiring immediate attention. If the patient is conscious and does not require medical attention, the patient may need to provide input to the WCD system 104 to prevent the defibrillator 108 from emitting a shock. If the patient is not conscious, the alert module 304 may alert bystanders to the severity of the situation and either provide direction to the bystanders of potential action to be taken or, in some instances, enable bystanders to contact medical support or emergency support as needed.

Figure 4:
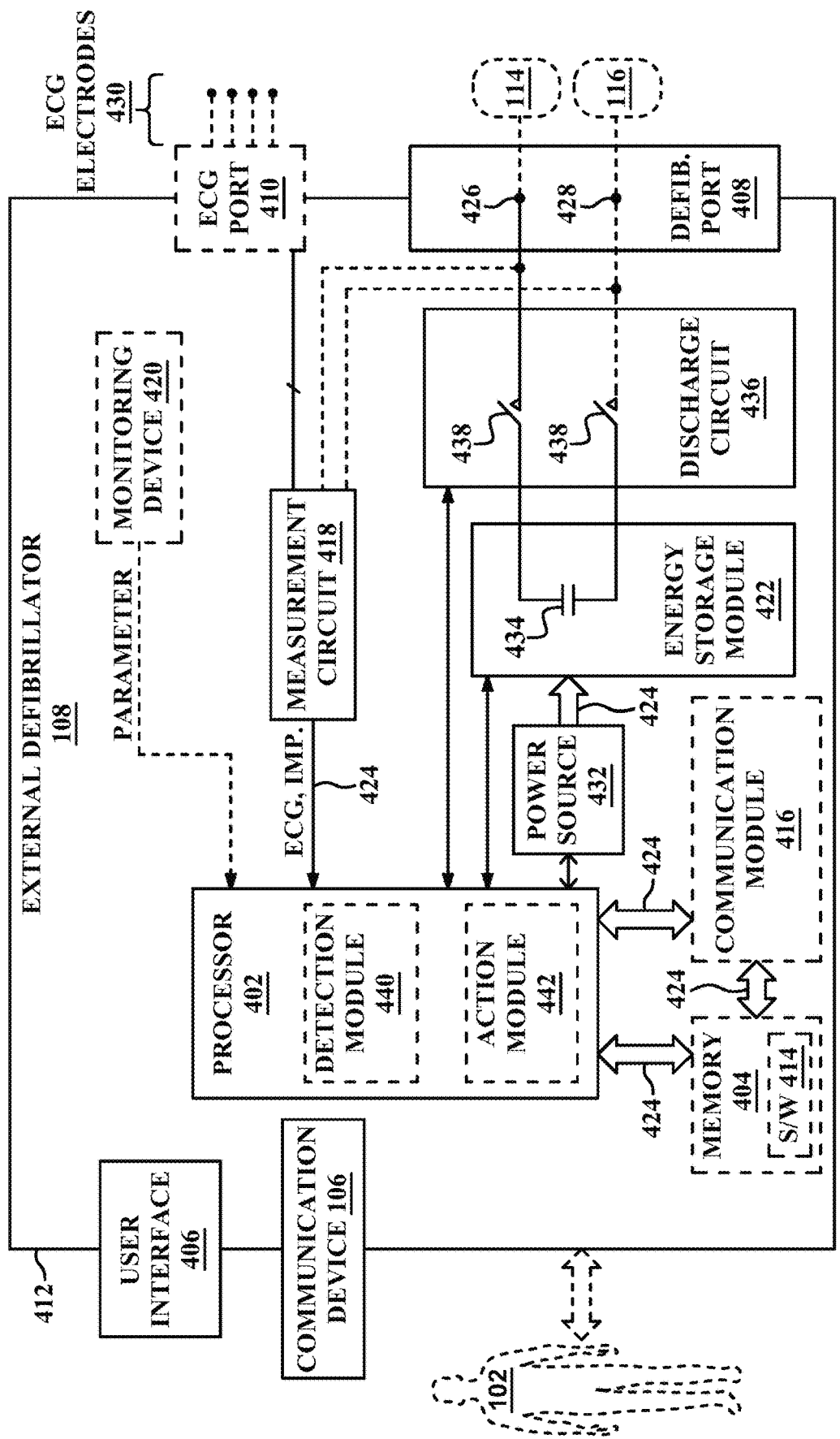
FIG. 4 is a block diagram of an example defibrillator in accordance with one example of the present disclosure.

FIG. 4 is a diagram displaying various components of an example external defibrillator 108. The external defibrillator 108 may be an example of the defibrillator 108 described with reference to FIG. 1. The components shown in FIG. 4 may be contained within a single unit or may be separated amongst two or more units in communication with each other. The defibrillator 108 may include a communication device 106, processor 402, memory 404, defibrillation port 408, and ECG port 410, among other components. In some embodiments, the components are contained within a housing 412 or casing. The housing 412 may comprise a hard shell around the components or may comprise a softer shell for increased patient comfort.

The communication device 106, processor 402, memory 404 (including software/firmware code (SW) 414), defibrillation port 408, ECG port 410, communication module 416, measurement circuit 418, monitoring device 420, and energy storage module 422 may communicate, directly or indirectly, with one another via one or more buses 424. The one or more buses 424 may allow data communication between the elements and/or modules of the defibrillator 108.

The memory 404 may include random access memory (RAM), read only memory (ROM), flash RAM, and/or other types. The memory 404 may store computer-readable, computer-executable software/firmware code 414 including instructions that, when executed, cause the processor 402 to perform various functions (e.g., determine shock criteria, determine consciousness of patient, track patient parameters, etc.). In some embodiments, the processor 402 may include an intelligent hardware device, e.g., a central processing unit (CPU), a microcontroller, an application-specific integrated circuit (ASIC), etc.

In some embodiments, the memory 404 can contain, among other things, the Basic Input-Output system (BIOS) which may control basic hardware and/or software operations such interactions and workings of the various components of the defibrillator 108, and in some embodiments, components external to the defibrillator 108. For example, the memory 404 may contain various modules to implement the workings of the defibrillator 108 and other aspects of the present disclosure.

In some embodiments, the defibrillator 108 may include a communication device 106. The communication device 106 may enable the patient to view one or metrics concerning the defibrillator 108. In some embodiments, the communication device 106 may include the components described with reference to FIG. 2. In some embodiments, the communication device 106 may be a part of the defibrillator 108 and share one or more internal components of the defibrillator. In other embodiments, as shown later in FIG. 5, the communication device 106 may be a removable component or separate component. In further embodiments, the defibrillator may include a separate user interface 406. The user interface 406 may be in addition to the communication device 106. The user interface 406 may display an ECG of the patient, a status of the defibrillator 108, a status of a charge (e.g., a battery charge or an energy storage module), and the like.

In some embodiments, the defibrillator 108 may include a defibrillation port 408. The defibrillation port 408 may comprise a socket, opening, or electrical connection in the housing 412. In some instances, the defibrillation port 408 may include two or more nodes 426, 428. The two or more nodes 426, 428 may accept two or more defibrillation electrodes (e.g., defibrillation electrodes 114, 116, FIG. 1). The nodes 426, 428 may provide an electrical connection between the defibrillation electrodes 114, 116 and the defibrillator 108. The defibrillation electrodes 114, 116 may plug into the two or more nodes 426, 428 via one or more leads (e.g., leads 118), or, in some instances, the defibrillation electrodes 114, 116 may be hardwired to the nodes 426, 428. Once an electrical connection is established between the defibrillation port 408 and the electrodes 114, 116, the defibrillator 108 may be able to deliver an electric shock to the patient 102.

In some embodiments, the defibrillator 108 may include an ECG port 410 in the housing 412. The ECG port 410 may accept one or more ECG electrodes 430 or ECG leads. In some instances, the ECG electrodes 430 sense a patient's ECG signal. For example, the ECG electrodes 430 may record electrical activity generated by heart muscle depolarization. The ECG electrodes 430 may utilize 4-leads to 12-leads or multichannel ECG, or the like. The ECG electrodes 430 may connect with the patient's skin.

In some embodiments, the defibrillator 108 may include a measurement circuit 418. The measurement circuit 418 may be in communication with the ECG port 410. For example, the measurement circuit 418 may receive physiological signals from ECG port 410. The measurement circuit 418 may additionally or alternatively receive physiological signals via the defibrillation port 408 when defibrillation electrodes 114, 116 are attached to the patient 102. The measurement circuit 418 may determine a patient's ECG signal from a difference in voltage between the defibrillation electrodes 114, 116.

In some embodiments, the measurement circuit 418 may monitor the electrical connection between the defibrillation electrodes 114, 116 and the skin of the patient 102. For example, the measurement circuit 418 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 420 within the housing 412. The monitoring device 420 may monitor at least one local parameter. Local parameters may include physical state of the patient such as ECG, movement, heartrate, pulse, temperature, and the like. Local parameters may also include a parameter of the WCD system (e.g., WCD 104, FIG. 1), defibrillator 108, environmental parameters, or the like.

In some embodiments, the WCD system 104 may include an internal monitoring device 420 and an external monitoring device (e.g., external monitoring device 124). If both monitoring devices 124, 420 are present, the monitoring devices 124, 420 may work together to parse out specific parameters depending on position, location, and other factors. For example, the external monitoring device 124 may monitor environmental parameters while the internal monitoring device 420 may monitor patient and system parameters.

In some embodiments, the defibrillator 108 may include a power source 432. The power source 432 may comprise a battery or battery pack, which may be rechargeable. In some instances, the power source 432 may comprise a series of different batteries to ensure the defibrillator 108 has power. For example, the power source 432 may include a series of rechargeable batteries as a prime power source and a series of non-rechargeable batteries as a secondary source. If the patient 102 is proximate an AC power source, such as when sitting down, sleeping, or the like, the power source 432 may include an AC override wherein the power source 432 draws power from the AC source.

In some embodiments, the defibrillator 108 may include an energy storage module 422. The energy storage module 422 may store electrical energy in preparation or anticipation of providing a sudden discharge of electrical energy to the patient. In some embodiments, the energy storage module 422 may have its own power source and/or battery pack. In other embodiments, the energy storage module 422 may pull power from the power source 432. In still further embodiments, the energy storage module 422 may include one or more capacitors 434. The one or more capacitors 434 may store an electrical charge, which may be administered to the patient. The processor 402 may be communicatively coupled to the energy storage module 422 to trigger the amount and timing of electrical energy to provide to the defibrillation port 408 and, subsequently, the patient.

In some embodiments, the defibrillator 108 may include a discharge circuit 436. The discharge circuit 436 may control the energy stored in the energy storage module 422. For example, the discharge circuit 436 may either electrical couple or decouple the energy storage module 422 to the defibrillation port 408. The discharge circuit 436 may be communicatively coupled to the processor 402 to control when the energy storage module 422 and the defibrillation port 408 should or should not be coupled to either administer or prevent a charge from emitting from the defibrillator 108. In some embodiments, the discharge circuit 436 may include one or more switches 438. The one or more switches 438 may include an H-bridge.

In some embodiments, the defibrillator 108 may include a communication module 416. The communication module 416 may establish one or more communication links with either local hardware and/or software to the WCD system 104 and defibrillator 108 or to remote hardware separate from the WCD system 104. In some embodiments, the communication module 416 may include one or more antennas, processors, and the like. The communication module 416 may communicate wirelessly via radio frequency, electromagnetics, local area networks (LAN), wide area networks (WAN), virtual private networks (VPN), RFID, Bluetooth, cellular networks, and the like. The communication module 416 may facilitate communication of data and commands such as patient data, episode information, therapy attempted, CPR performance, system data, environmental data, and so on.

In some embodiments, the processor 402 may execute one or more modules. For example, the processor 402 may execute a detection module 440 and/or an action module 442. The detection module 440 may be a logic device or algorithm to determine if any or a variety of thresholds are exceeded which may require action of the defibrillator 108. For example, the detection module 440 may receive and interpret all of the signals from the ECG port 410, the defibrillation port 408, the monitoring device 420, an external monitoring device, and the like. The detection module 440 may process the information to ensure the patient is still conscious and healthy. The detection module 440 may communicate with the communication device 106 or be a part of the communication device 106. For example, the detection module 440 may be the same as detection module 302 or may communicate with the detection module 302. If any parameter indicates the patient 102 may be experiencing distress or indicating a cardiac episode, the detection module 440 may activate the action module 442. Similarly, either detection module 440, or detection module 302 may trigger the alert module 304.

The action module 442 may receive data from the detection module 440 and perform a series of actions. For example, an episode may merely be a loss of batter power at the power source 432 or the energy storage module 422, or one or more electrodes (e.g., ECG electrodes, defibrillation electrodes) may have lost connection. In such instances, the action module 442 may trigger an alert to the patient or to an outside source of the present situation. This may include activating the alert module 304 of the communication device 106 if the alert module 304 has not already been activated. If an episode is a health risk, such as a cardiac event, the action module 442 may begin a series of steps. This may include issuing a warning to the patient, issuing a warning to a third party, priming the energy storage module 422 for defibrillation, releasing one or more conductive fluids proximate defibrillation electrodes 114, 116, and the like.

Figure 5:
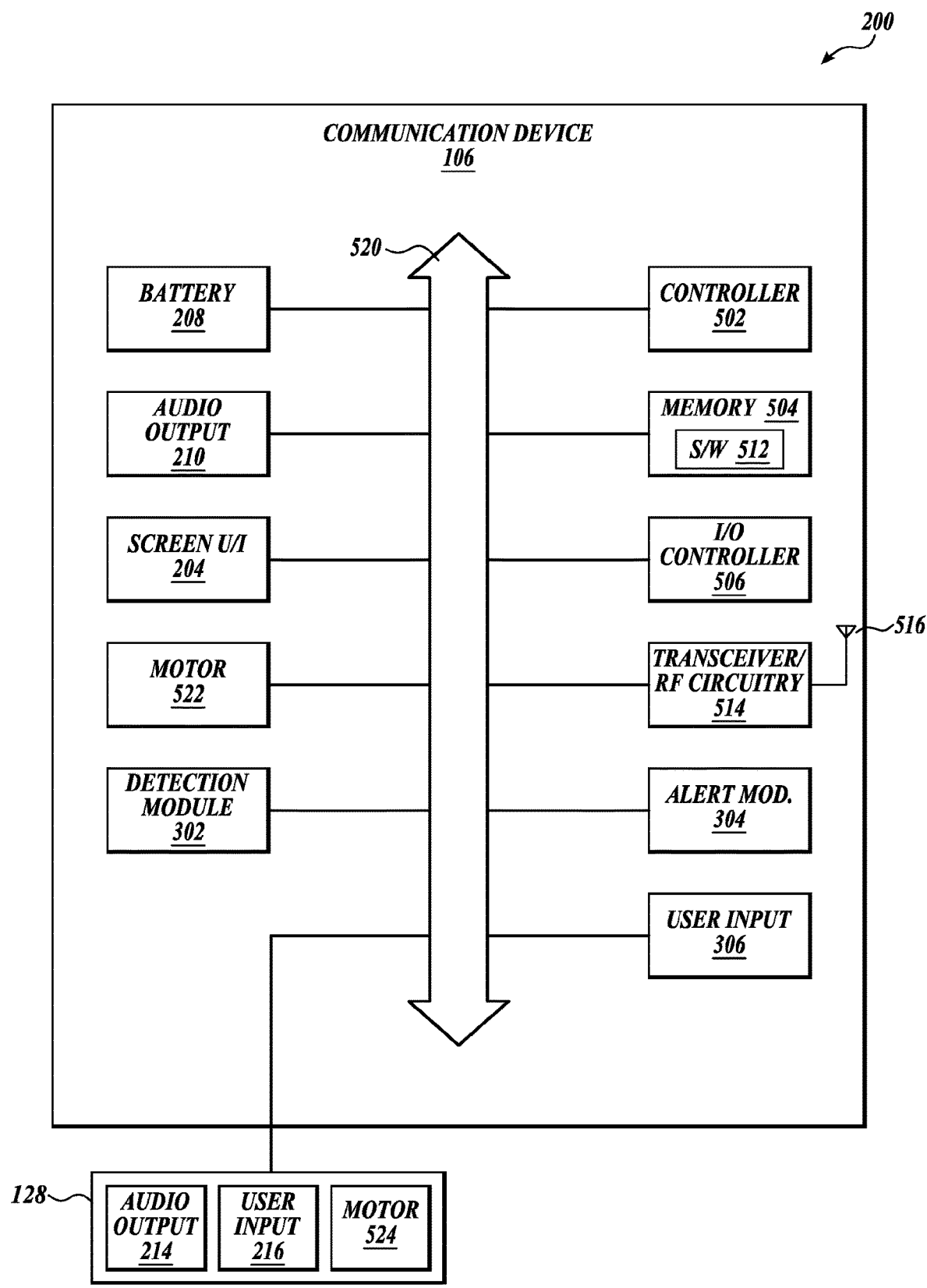
FIG. 5 is a block diagram of an example communication system in accordance with one example of the present disclosure.

FIG. 5 is a diagram displaying various components of an example communication system 200 for use with a WCD system 104. The communication system 200 may include a communication device 106 and an alert button 128. The communication device 106 and alert button 128 may be an example of the communication device 106 and alert button 128 described with reference to FIGS. 1 and 2. The communication system 200 may be coupled to the defibrillator 108 or may include separate components communicatively coupled to the defibrillator 108. In some embodiments, the communication device 106 may include a controller 502, memory 504, I/O controller 506, and the like.

The controller 502, memory, 504 (including software/firmware code (SW) 512), input/output controller module 506, a transceiver module 514, and one or more antennas 516 may communicate, directly or indirectly, with one another via one or more buses 520. The transceiver module 514 may communicate bi-directionally, via the one or more antennas 516, wired links, and/or wireless links, with the defibrillator 108 or remote devices 126 as described previously. The transceiver module 514 may include a modem which may modulate packets and provide the modulated packets to the one or more antennas 516 for transmission, and to demodulate packets received from the one or more antenna 516. While a single antenna 516 is shown, the communication device may include several antennas 516 which may concurrently transmit and/or receive multiple wired and/or wireless transmissions. In some embodiments, the communication device 106 may provide a connection using wireless techniques, including digital cellular connection, Cellular Digital Packet Data (CDPD) connection, digital satellite data connection, and/or another connection.

The controller 502 may control one or more operations of the communication device 106. The controller 502 may include one or more processors, implemented as a Central Processing Unit (CPU), a digital signal processor, a microprocessor, a microcontroller, an application-specific integrated circuit (ASIC), a programmable logic device (PLD), or other implementation. In some embodiments, the controller 502 may include a single chip combined with memory controller and a peripherals interface.

The memory 504 may be a non-transitory computer-readable storage medium. In some embodiments, the memory 504 may include both persistent/non-volatile and non-persistent/volatile memory components. The memory 504 may include volatile memory, non-volatile memory (NVM), for example RAM, ROM, EEPROM, flash memory, or some combination thereof. The memory 504 may store computer-readable, computer executable software/firmware code 512 that, when executed, may cause the controller 502 to perform various functions as described herein.

In some embodiments, the memory 504 can contain, among other things, the Basic Input-Output system (BIOS) which may control basic hardware and/or software operations such interactions and workings of the various components of the communication device 106, and in some embodiments, components external to the communication device 106. For example, the memory 504 may contain various modules to implement the workings of the communication system 200 and other aspects of the present disclosure.

The communication device 106 may also include components for bi-directional voice and data communications including components for transmitting communications and components for receiving communications. For example, the communication device 106 may communicate bi-directionally with the defibrillator 108, the WCD system 104, and/or external devices 124. The bi-directional communication may be direct or indirect.

The input output controller (I/O controller) 506 may coordinate communication with the patient. For example, the I/O controller 506 may receive inputs from the user and also may generate outputs to the user. The I/O controller 506 may interface with the audio output 210, visual indicator 206, screen 204, and a motor 522 of the communication device 106. The I/O controller 506 may also interface with the audio output 210, user input 216, and motor 524. The I/O controller 506 may coordinate with the alert module 304 to activate various user outputs to provide an alarm or to communicate with the patient. The I/O controller 506 may also coordinate with the user input 216 to receive patient feedback via the user input 216.

The audio outputs 210, 214 may each include a speaker. The output of the audio outputs 210, 214 may be loud enough to be heard over nominal background noise. The visual indicator 206 may include one or more light sources. The visual indicator 206 may indicate an alarm presence and severity using colors and patterns with optical communication. The screen 204 may include any variation of a screen to display text and images to a patient and/or user.

The motors 522, 524 may be one of a flat coin vibrating vibration motor, DC vibration motor, haptic actuator, eccentric rotating mass (ERM) vibration motor, cylindrical vibration motor, q-coin vibration motors, PCB vibration motor, pancake vibration motor, linear resonant actuator (LRA), piezo actuator, and the like. The motor 522 of the communication device 106 and the motor 524 of the alert button 128 need not be the same in size or programming. The motor selected for each case may be best suited for the size of the device requiring vibration and the output necessary given the size of the device. For example, the motor 524 coupled to the alert button 128 may be smaller than the motor 522 for the communication device 106 because the alert button 128 is smaller. In other embodiments, the motors 522, 524 may be the same. In either situation, the motors 522, 524 may be programmed alike or differently. For example, the force of the vibration at the communication device 106 may be different than the force at the alert button 128. While the overall output may appear similar to the patient, the input may be different to achieve that result.

The detection module 302, alert module 304, and user input module 306 may perform similar functions as the detection module 302, alert module 304, and user input module 306 described with reference to FIG. 2.

In some embodiments, the communication device 106 may include a battery 208. The battery 208 may be a single battery or battery pack, which may be rechargeable. In some instances, the battery 208 may comprise a series of different batteries to ensure the communication device 106 has power. For example, the battery 208 may include a series of rechargeable batteries as a prime power source and a series of non-rechargeable batteries as a secondary source. If the patient 102 is proximate an AC power source, such as when sitting down, sleeping, or the like, the battery 208 may include an AC override wherein the battery 208 draws power from the AC source.

Figure 6:
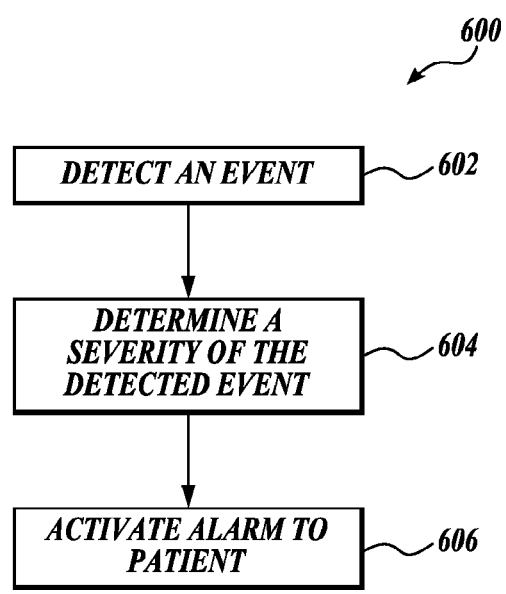
FIG. 6 is a flow diagram illustrating an example of a method for alerting a patient in accordance with the present disclosure.

FIG. 6 is a flow chart illustrating an example of a method 600 for WCD systems, in accordance with various aspects of the present disclosure. For clarity, the method 600 is described below with reference to aspects of one or more of the systems described herein.

At block 602, the method 600 may include detecting an event. The event may be any type of event or disruption at the WCD systems. The event may be one that requires patient intervention, such as adjusting a sensor, electrode, or other component of the WCD system. The event may require charging the system or the defibrillator. The event may also be more serious such as detection of a cardiac event, irregular heartbeat, arrhythmia, or the like.

At block 604, the method 600 may include determining a severity of the detected event. The severity may be measured on a predetermined basis. For example, potential failure modes of the WCD system 104 may be preprogrammed into a severity event chart. This made include potential consequences if the event is not remedied and a duration that remedy needs to occur. For example, a low battery may not be immediately severe but as a time duration of low battery power lengthens, the severity of charging the unit becomes higher. Likewise, limited ECG sensor contact may not be an emergency but may need remediation to garnish accurate ECG readings. A first detection of limited contact may be a lower or medium level alert. A continued detection may increase the severity level of the alert.

At block 606, the method 600 may include activating an alarm to a patient. The severity and amount of alarm components may vary based on the severity level of the detected event. For example, the alarm may include one of an audible alarm, visual alarm, tactile alarm, or a combination thereof. The alarm itself may be a collective combination of the audible, visual, and tactile alarm distributed to the patient. The alarm may begin with one of the three types of alarms and then slowly increase the perceptibility of the alarm.

In some embodiments, the visual alarm may activate first for a predetermined period of time. The visual alarm may include a blinking light and a visual message to the patient. After the predetermined time period, the tactile alarm may combine with the visual alarm to increase the perceptibility of the alarm. Again, after a predetermined time period, if the patient does not respond to the alarm, the alarm may add an audible component. The three alarm components may continue to increase in severity until the patient acknowledges the alarm. The severity may include a volume of the alarm, a brightness of the light, an increase in vibrational energy, or a combination thereof.

The predetermined time period between activating various alarm components and increasing the perceptibility of the components may vary based on the severity of the event. For example, in a low-level priority event, the predetermined time period may be longer than for a high priority event. The low-level priority event may have a predetermined time period ranging from thirty seconds to several minutes. The duration of the predetermined time period may be personalized to the user. In a high priority event, the duration of the predetermined time period may be negligible. For example, each component of the alarm may activate at once and a severity of the alarm components may increase quickly. Medium priority events may vary somewhere in between the low-level priority events and the high-priority events.

In still further embodiments, emergency situations may have more urgent alarm protocols. Emergency situations may arise when a cardiac event is detected, an impending shock is being prepared, a high alert alarm has gone unanswered or other situations that may occur. The emergency alarms may be a higher discernibility than the rest of the alarms. A high discernibility may be a higher volume, higher tactile strength, brighter visual aids. A high discernibility may also comprise a completely separate alarm which may indicate to the user or to bystanders that a distinct emergency event is occurring. The emergency alarm may provide commands or announcements to surrounding bystanders to aid in the safety of the patient. For example, if a shock is impending, the alarm may announce the shock and ask bystanders to clear the patient. The alarm may provide additional information dependent upon the situation.

Thus, the method 600 may provide for alerting a patient. It should be noted that the method 600 is just one implementation and that the operations of the method 600 may be rearranged or otherwise modified such that other implementations are possible.

Figure 7:
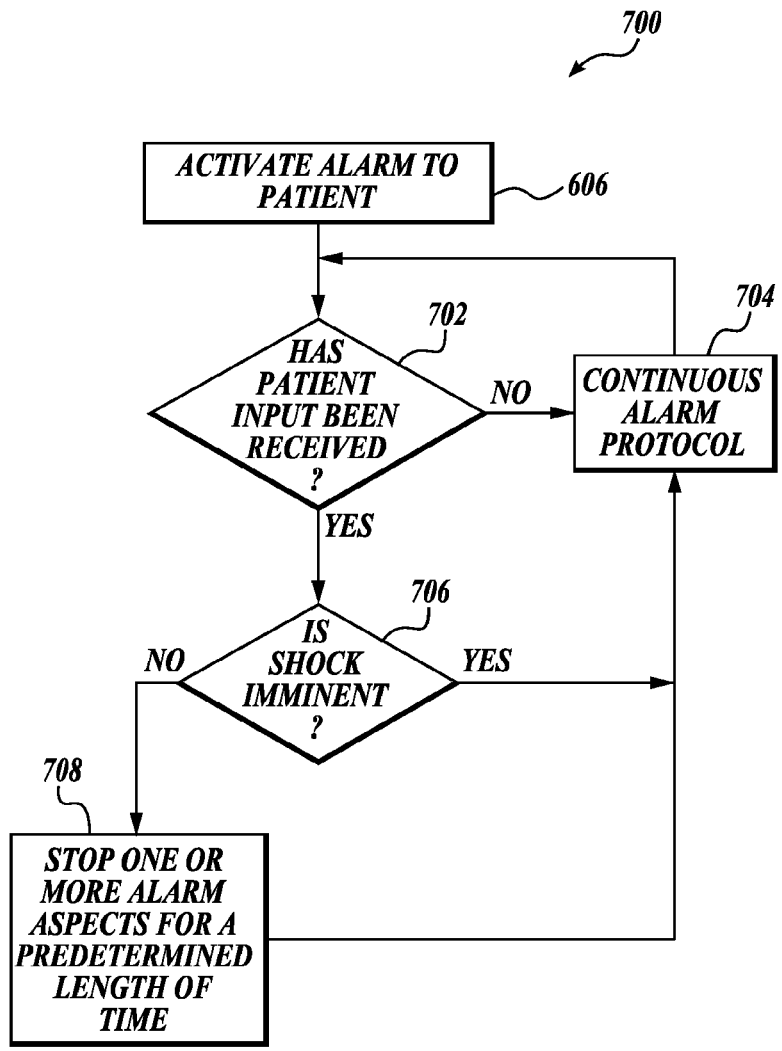
FIG. 7 is a flow diagram illustrating another example of a method for alerting a patient in accordance with the present disclosure.

FIG. 7 is a flow chart illustrating an example of another method 700 for WCD systems, in accordance with various aspects of the present disclosure. For clarity, the method 700 is described below with reference to aspects of one or more of the systems described herein.

At block 606, the method 700 may include activating an alarm to the patient.

At block 702, the method 700 may include determining if patient input is received. The patient input may include a patient snoozing or deactivating an alarm. For example, if a patient does not wish for a noise to be heard, the patient may silence the alarm. If patient input has not been received, at block 704 the method 700 may include continuing alarm protocol. In various embodiments, the alarm protocol depends upon the alarm severity.

At block 706, if the patient has snoozed the alarm, the method 700 may include determining if a shock is eminent. If a shock is eminent, but the patient has snoozed the alarm, the method 700, at block 704, may continue the alarm protocol. For example, the patient may be conscious and experiencing a false positive shock criterion. If the patient has snoozed the alarm, the patient may not be aware that a shock is imminent and may experience the shock. However, if the alarm protocol is continued, the patient may be alerted to a more pressing alarm situation, if the patient is conscious. Similarly, if the alarm snooze button has been activated either accidentally or by a third party, the alarm protocol may alert the patient, or the bystander that the alarm severity is high.

If a shock is not eminent, at block 708, the method 700 may cease one or more of the alarm components for a predetermined length of time. The predetermined length of time may depend upon event severity. Similarly, if the event severity increases, the predetermined length of time may be truncated. Once the predetermined amount of time has passed, at block 704, the method 700 may continue alarm protocols.

Thus, the method 700 may provide for alerting a patient. It should be noted that the method 700 is just one implementation and that the operations of the method 700 may be rearranged or otherwise modified such that other implementations are possible.

Figure 8:
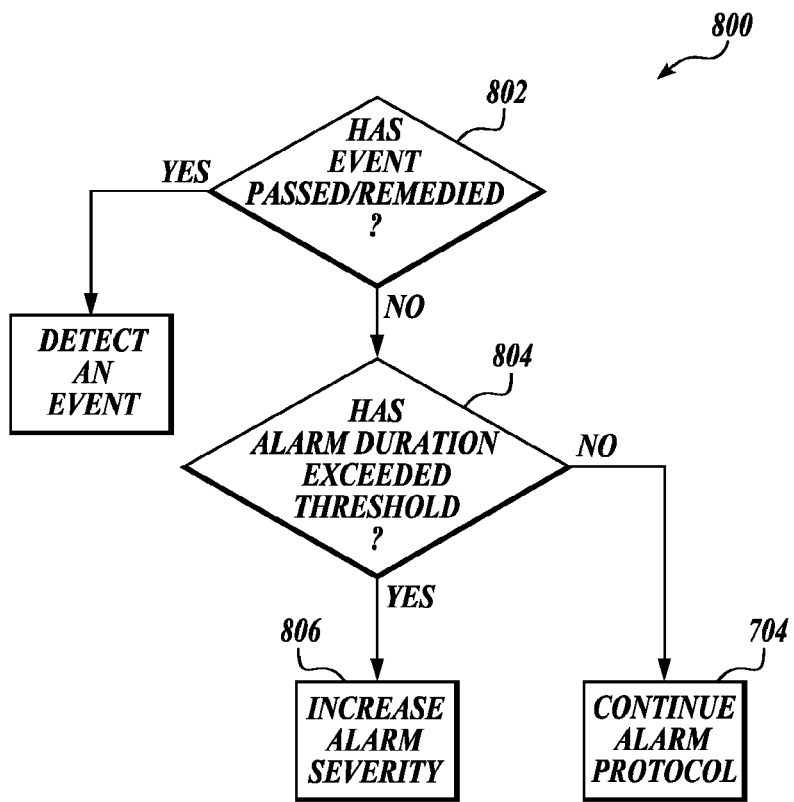
FIG. 8 is a flow diagram illustrating another example of a method for alerting a patient in accordance with the present disclosure.

FIG. 8 is a flow chart illustrating an example of a method 800 for WCD systems, in accordance with various aspects of the present disclosure. For clarity, the method 800 is described below with reference to aspects of one or more of the systems described herein.

At block 802, the method 800 may include determining if an event has passed or been remedied. If the event has been remedied, or has passed, the method 800 may, at block 602, continue detecting or searching for an event.

If the event has not passed or not been remedied, at block 804, the method 800 may determine if a duration of the alarm has exceeded a threshold. The threshold may be a predetermined amount of time or may be a predetermined number of times the alarm has been snoozed. The threshold may vary depending on event severity. For example, a more severe event may have a shorter time threshold than a lower priority event.

If the threshold has been exceeded, at block 806, the method 800 may increase an alarm severity. This may include increasing the perceptibility of the alarm. This may mean increasing the volume of the sound, pitch, or tone of the audible alarm. In some embodiments, the method 800 may change the actual sound itself to a more urgent note. The haptic alarm may increase in strength. The visual alarm may become brighter.

However, if the threshold has not been exceeded, at block 704, the method 800 may continue alarm protocols. The alarm protocols may be ordinary protocols to follow given the severity of the alarm.

Thus, the method 800 may provide for alerting a patient. It should be noted that the method 800 is just one implementation and that the operations of the method 800 may be rearranged or otherwise modified such that other implementations are possible.

This document may include references to directions, such as "forward," "rearward," "front," "rear," "upward," "downward," "top," "bottom," "right hand," "left hand," "lateral," "medial," "in," "out," "extended," etc. These references, and other similar references, are only to assist in helping describe and to understand the particular embodiments and are not intended to limit the present disclosure to these directions or locations.

The present document may also reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

While illustrative embodiments have been illustrated and described, it will be appreciated that various changes can be made therein without departing from the spirit and scope of the disclosure.

We claim:

1. A wearable cardioverter defibrillator (WCD) including a support structure configured to be worn by a patient, the WCD comprising:
at least one communication device, the at least one communication device configured to output a first part of a multi-sensory alarm, the multi-sensory alarm including at least a specific lighting pattern determined by an event displayed on the at least one communication device and/or an alert button;
the alert button configured to output a second part of the multi-sensory alarm and to detect patient input; and
a processor configured to:
detect the event occurring at the WCD;
generate the multi-sensory alarm based at least in part on the detected event;
in response at least in part to the detected event, cause the multi-sensory alarm to be output by the at least one communication device and by the alert button;
determine an urgency of the detected event; and
modify the multi-sensory alarm based on the urgency of the detected event, wherein modifying the multi-sensory alarm includes at least modifying a brightness of the specific lighting pattern.

2. The WCD of claim 1, wherein the first part of the multi-sensory alarm comprises a visual alarm, or a haptic alarm, or an audible alarm, or any combination of such alarms.

3. The WCD of claim 2, further comprising a microphone configured to:
detect ambient noise; and
modify a volume of the audible alarm based on the ambient noise detected.

4. The WCD of claim 1, wherein the second part of the multi-sensory alarm comprises a combination of at least two of a visual alarm, an audible alarm, or a haptic alarm.

5. The WCD of claim 4, wherein the processor is further configured to:
harmonize at least two of the visual alarm, audible alarm, and haptic alarm output by each of the at least one communication device and the alert button.

6. The WCD of claim 1, wherein the processor is further configured to:
receive the patient input from the alert button; and
modify the multi-sensory alarm based on the patient input.

7. The WCD of claim 6, wherein the multi- sensory alarm is modified to change at least one of intensity, tempo, volume, and a length of the multi-sensory alarm.

8. The WCD of claim 6, wherein the processor is further configured to:
determine a no urgency of the detected event; and
cease the first part of the multi-sensory alarm and the second part of the multi-sensory alarm for a predetermined length of time based on the no urgency of the detected event,
wherein the predetermined length of time is determined based on a severity of the detected event.

9. A wearable cardioverter defibrillator (WCD) system, including a support structure configured to be worn by a patient, the WCD system comprising:
a defibrillator housing;
at least one communication device configured to output a first part of a multi-sensory alarm;
an alert button coupled to the support structure and configured to output a second part of the multi-sensory alarm and to detect a patient input, the multi-sensory alarm including at least a lighting pattern determined by an event displayed on the at least one communication device and/or the alert button; and
a processor configured to:
detect the event occurring at the WCD,
generate the multi-sensory alarm based at least in part on the detected event;
in response at least in part to the detected event, cause the multi-sensory alarm to be output by the at least one communication device and by the alert button in a harmonic manner;
determine an urgency of the detected event; and
modify the first part or the second part of the multi-sensory alarm based on the urgency of the detected event, wherein modifying the multi-sensory alarm includes at least modifying a brightness of the lighting pattern.

10. The WCD system of claim 9, wherein the first part of the multi-sensory alarm comprises a visual alarm, or a haptic alarm, or an audible alarm, or any combination of such alarms.

11. The WCD system of claim 10, further comprising a microphone configured to:
   detect ambient noise; and
   modify a volume of the audible alarm based on the ambient noise detected.

12. The WCD system of claim 9, wherein the second part of the multi-sensory alarm is a combination of at least two of a visual alarm, an audible alarm, or a haptic alarm.

13. The WCD system of claim 12, wherein the processor is further configured to:
   harmonize at least two of the visual alarm, audible alarm, and haptic alarm output by each of the at least one communication device and the alert button.

14. The WCD system of claim 9, wherein the processor is further configured to:
   receive the patient input from the alert button; and
   modify the multi-sensory alarm based on the patient input.

15. The WCD system of claim 14, wherein the multi-sensory alarm is modified to change at least one of intensity, tempo, volume, and a length of the multi-sensory alarm.

16. The WCD system of claim 14, wherein the processor is further configured to:
   determine a no urgency of the detected event; and
   cease the first part of the multi-sensory alarm and the second part of the multi-sensory alarm for a predetermined length of time based on the no urgency of the detected event,
   wherein the predetermined length of time is determined based on a severity of the detected event.

17. A wearable cardioverter defibrillator (WCD) system including a support structure configured to be worn by a patient, the WCD system comprising:
   one or more electrodes for delivering a charge to the patient, while the patient is wearing the support structure;
   a discharge circuit coupled to the one or more electrodes, the discharge circuit configured to store an electrical charge;
   a communication device configured to output a first part of a multi-sensory alarm, the multi-sensory alarm including at least a specific lighting pattern determined by an event displayed on the at least one communication device and/or an alert button;
   the alert button in communication with the processor, the alert button comprising a second part of the multi-sensory alarm; and
   the processor configured to:
      cause the discharge circuit to discharge the stored electrical charge through the one or more electrodes in response to one or more shock criteria being met;
      detect the event occurring at the WCD;
      generate the multi-sensory alarm based at least in part on the detected event;
      in response at least in part to the detected event, cause the first part of the multi-sensory alarm and the second part of the multi-sensory alarm to be output by the communication device and by the alert button;
      determine an urgency of the detected event; and
      modify the multi-sensory alarm based on the urgency of the detected event, wherein modifying the multi-sensory alarm includes at least modifying a brightness of the specific lighting pattern.

18. The WCD system of claim 17, wherein the second part of the multi-sensory alarm is a combination of at least two of a visual alarm, an audible alarm, or a haptic alarm.

19. The WCD system of claim 18, wherein the processor is further configured to:
   harmonize at least two of the visual alarm, audible alarm, and haptic alarm output by each of the communication device and the alert button.

20. The WCD system of claim 17, wherein the processor is further configured to:
   receive user input from the alert button; and
   modify the multi-sensory alarm based on the user input.

* * * * *